Figure 1:
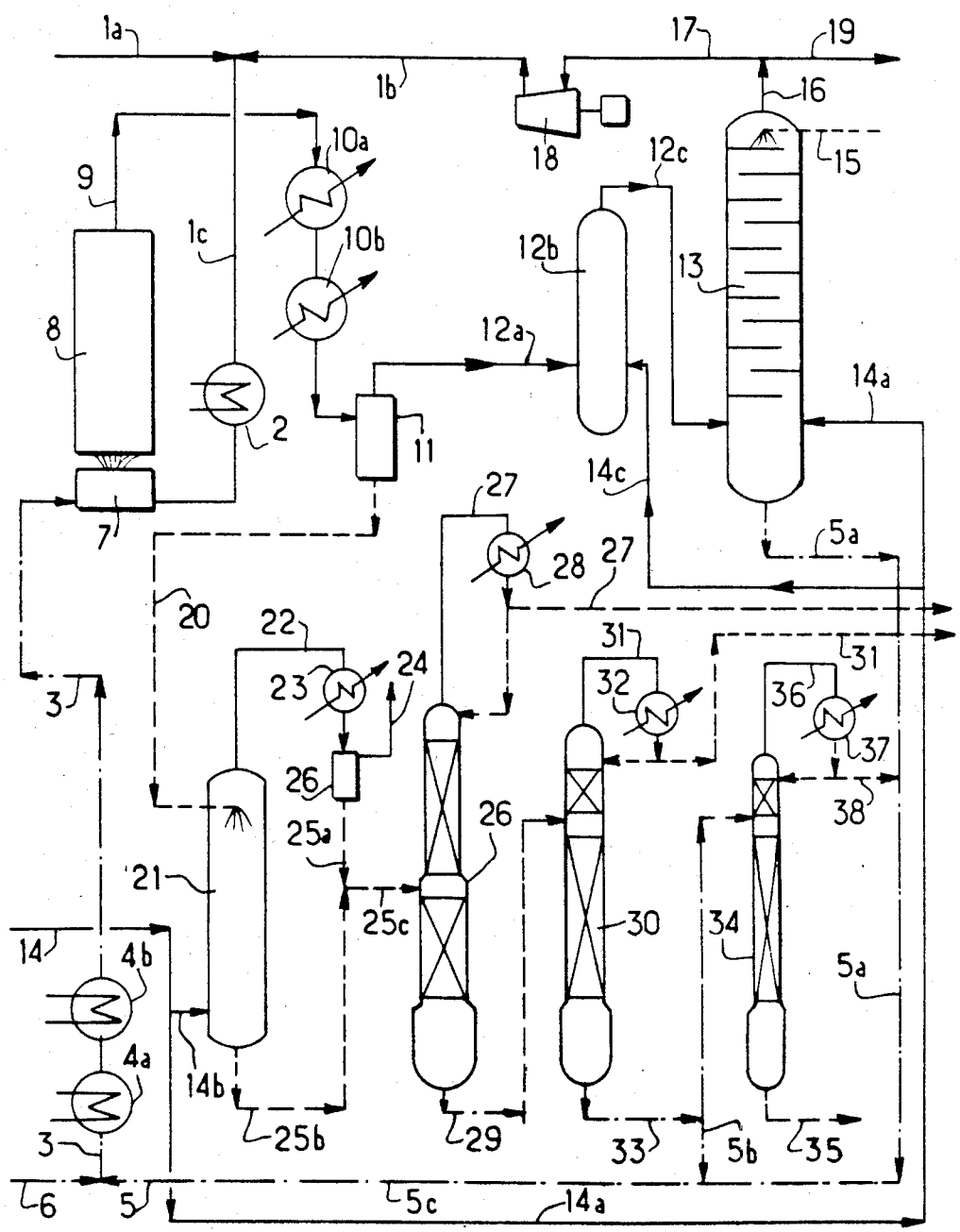

United States Patent [19]

Jacquinot et al.

[11] Patent Number: 4,626,607

[45] Date of Patent: Dec. 2, 1986

[54] PROCESS AND INSTALLATION FOR MANUFACTURING NITROMETHANE

[75] Inventors: Bernard Jacquinot, Douai; Jacques Quibel, Maisons Laffitte; Roger Mari, Villers-les-Nancy, all of France

[73] Assignee: Societe Chimique de la Grande Pariosse, Azote et Produits Chimiques, Paris, France

[21] Appl. No.: 695,047

[22] Filed: Jan. 25, 1985

[30] Foreign Application Priority Data

Jan. 27, 1984 [FR] France ............................. 84 01248

[51] Int. Cl.$^4$ ............................................. C07C 79/04
[52] U.S. Cl. ................................. 568/948; 260/688
[58] Field of Search .................... 260/688; 568/948

[56] References Cited

U.S. PATENT DOCUMENTS

| | | | |
|---|---|---|---|
| 2,161,475 | 6/1939 | Landon | 260/644 |
| 2,164,774 | 7/1939 | Landon | 260/644 |
| 2,291,345 | 7/1942 | Rideout | 260/644 |
| 2,418,241 | 4/1947 | Stengel et al. | 260/644 |
| 2,512,587 | 6/1950 | Stengel | 260/644 |
| 2,597,698 | 5/1952 | Bachman et al. | 260/644 |
| 2,885,447 | 5/1959 | McKinnis et al. | 568/948 |
| 3,470,251 | 9/1969 | Siegart et al. | 260/583 |
| 3,470,252 | 9/1969 | Doyle et al. | 564/494 |
| 3,780,115 | 12/1973 | Lhonore et al. | 568/947 |
| 3,869,253 | 3/1975 | Lhonore et al. | 422/189 |
| 4,260,838 | 4/1981 | Lhonore et al. | 568/947 |
| 4,313,009 | 1/1982 | Lhonore et al. | 568/947 |
| 4,313,010 | 1/1982 | Lhonore et al. | 568/948 |
| 4,329,523 | 5/1982 | James et al. | 568/948 |
| 4,458,094 | 7/1984 | Sherwin | 568/948 |

*Primary Examiner*—Stephen J. Lechert, Jr.
*Assistant Examiner*—Anne Brookes
*Attorney, Agent, or Firm*—Browdy and Neimark

[57] ABSTRACT

The invention concerns the manufacture of nitromethane by nitration of methane in a homogeneous gaseous phase, the nitrating agent being nitric acid, nitrogen peroxide or mixtures thereof. According to the disclosed process, the molar ratio methane/nitrating agent is between 0.1 and 5; the reaction contact time between 0.1 and 120 seconds; the reaction pressure between 1 and 35 bars; the temperature between 270° and 600° C. The nitration is carried out in the presence of an active agent of the halogen or derivative type introduced in a molar ratio at the most equal to 3. An installation is disclosed for industrially manufacturing nitromethane.

17 Claims, 2 Drawing Figures

PROCESS AND INSTALLATION FOR MANUFACTURING NITROMETHANE

The present invention relates to the manufacture of nitromethane or mixtures of nitroparaffins having a high nitromethane content.

Various processes have been proposed for manufacturing nitroparaffins from aliphatic hydrocarbons, in particular propane, ethane and mixtures. However, these techniques do not solve in the best way the present problem of the industrial production of nitroparaffins. In order to reach a satisfactory degree of profitability, a spectrum of nitroparaffins adapted to the needs of the market must be produced while employing raw materials which are cheap and available in large quantities. Moreover, it is essential to limit the specific overall consumption of hydrocarbons which takes into account both the consumption in the reactor and the loss of hydrocarbons in the recovery operation.

Even though the use of ethane or ethane-propane mixtures according to the U.S. Pat. Nos. 4,260,838, 4,313,009 and 4,313,010 provide means for increasing the nitromethane content in the nitroparaffins produced, it has been found that the direct nitration of the methane should constitute a more advantageous solution than the foregoing solutions.

However, it is well known that methane is much less energy to nitrate than heavier nitrocarbons owing to its greater stability—and consequently the greater difficulty to break the carbon-hydrogen bond—and to the greater fragility of the nitromethane molecule which is liable to be decomposed in the reactor after its formation. The previous works disclosed in the U.S. Pat. Nos. 2,161,475, 2,164,774, 2,418,241, 2,512,587 and 4,329,523 teach the conditions of nitration of methane. However, the rates of conversion of the methane into nitromethane are always low; the maximum conversion, obtained by introducing nitric acid at several points, did not exceed 7%.

Owing to a delicate recovery of the methane which has not reacted in the reactor, the high hydrocarbon/nitrating agent ratios (minimum 8 in molar ratio) and small conversions of the methane into nitromethane, the methods of the prior art have not led to a specific overall consumption of methane which is small enough to contemplate an industrial exploitation.

The art has searched for a process for nitrating methane, or a mixture of hydrocarbons containing a substantial quantity of methane, such as natural gases or refinery gases, by a nitration agent, providing a high rate of conversion and a residual quantity of methane which is low enough to avoid methane recovery.

It has now been found according to the invention that, in order to obtain the expected yields and conversions, the quantitative ratios of the various reagents. the reaction contact time, the temperature and the pressure of nitration are so chosen and controlled that the whole of the reactive mixture: hydrocarbon, nitrating agent and other possible constitutents, is employed in a homogeneous gaseous phase.

The nitrating agent is nitric acid and nitrogen peroxide used alone or in a mixture. The nitric acid may have a concentration of between 30 and 100%, and more advantageously 65 to 100%. Industrial nitric acid having a maximum concentration of 60 to 65% may be used.

The choice of the methane-nitrating agent molar ratio has an influence on the results advantageously this ratio must be between 0.1 and 5 and preferably between 0.2 and 2.

The reaction contact time is a function of the temperature, the pressure and the methane/nitrating agent ratio and is advantageously between 0.1 and 120 seconds and preferably between 5 and 30 seconds.

The nitration pressure is maintained between 1 and 35 bars absolute and preferably between 2 and 10 bars with nitro acid and 5 to 30 bars absolute with nitrogen peroxide.

The reaction temperatures are between 270° C. and 600° C. and preferably between 300° and 480° C. They are strictly controlled by suitable means so as to ensure a thermal transfer.

To carry out the process, the reagents are preheated to a controlled temperature at the most equal to the reaction temperature; the nitrating agent is preheated separately from the methane or the mixture of hydrocarbons containing a substantial quantity of methane, such as natural gas or refinery gas, and reagents are mixed at a temperature at the most equal to the temperature of the reaction and at a point which is the closest to the reactive zone and in the most homogeneous manner possible.

Further, it has been found that the rate of conversion of the methane into nitromethane may be improved by the addition of active agent in the course of the nitration. The active agent participating in the nitration is introduced at a rate of supply which is such that the active agent/nitrating agent molar ratio does not exceed 3: this ratio is adjusted as a function of economical criteria at its optimum value.

The halogens, in particular chlorine and bromine and their halogenated derivatives such as hydracids like hydrochloric acid; the organic halides such as the alkyl bromides and chlorides, mono- or polyhalogenated, or mono- or polyhalogenated olefin halides capable of being vaporized under the conditions of the reaction, constitute preferred active agents, which may be likened to homogeneous catalysts. Any saturated or non-saturated arylic or aliphatic organic halide is suitable for this purpose.

If hydrochloric acid, chlorinated compounds and chlorine have closely similar behaviors and consequently a comparable influence, the brominated, iodinated and fluorinated derivatives, according to their stability, have sometimes a less determinent action. There may be mentioned in addition methylene chloride, trichloromethane, methyl iodide, ethyl chloride, ethyl bromide, propyl chloride and isopropyl chloride, isoamyl fluoride, benzyl chloride, dichloro- and tetrachloroethylene, mono-, di-, trichlorethane and carbon tetrachloride.

The action of the active agent on the rate of conversion or yield is substantial, interesting and advantageous when the active agent is introduced in an active agent/methane roller ratio at the most equal to 3.

Depending on its chemical nature, the active agent is introduced into the reactive medium mixed with the reagent in respect of which it has a neutral behavior. Depending on the possible reactions between the active agent and one of the reagents, which should be avoided, said active agent will be introduced either with the nitrating agent or with the hydrocarbon.

The halogenated active agent must be vaporizable with one of the reagents or capable of being put in solution in an organic or aqueous solvent.

The use of the active agent in solution in a suitable solvent results in conversions which are at least equal to those which could be obtained with the active agent used in the pure state. This is of particular interest when using industrial nitric acid (maximum concentration 60–65%) as the nitrating agent.

Other compounds, such as the carriers of NO or $NO_2$ groups, the aldehydes, the ketones or certain alcohols may be used either individually or in association with the aforementioned chlorinated compounds. The nitroparaffins, such as the nitropropanes, contribute to the improvement of the conversion.

Further, under certain conditions, the nitration reaction may be facilitated by the addition one or more constituents which are inert with respect to the reaction and the reacted products. The inert constituent may be a gas, a gaseous mixture or a volatile liquid. The chosen use of diluted nitric acid permits the introduction of the inert constitutent in the form of water of dilution and additionally effects a reduction in the cost of the nitrating agent. The recycling of a part of the non-condensable fraction of the effluents of the reactor—after adequate purifications—also permits the use of carbon oxides, formed in the course of the reaction, as an inert constituent.

The inert constitutent may be chosen from gases such as nitrogen, carbon monoxide, carbon dioxide, hydrogen or a mixture of these gases, from vaporizable liquids such as vapours of organic compounds or steam coming from the dilution of the nitric acid, or from a mixture of these gases and these vapours.

The process according to the invention permits an industrial exploitation satisfying economic requirements.

The reactor is the centre of the nitration and all the parameters of the reaction: temperature, pressure, methane/nitrating agent ratios, flow of active agent, content of inert gases, composition of the mixture employed as active agent, are controlled with precision; the possibilities of thermal exchange within the reactor are sufficient to evacuate the heat given off correctly.

The gas rich in methane containing the inert constitutents, and the nitrating agent, are preheated before they are put into reaction. The active agent is added either in the nitrating agent where such active agent is hydrochloric acid, or in the gas rich in methane for a halogenated organic compound or mixture.

It has been found to be advantageous to recover the thermal energy of the effluents of nitration in the course of the cooling of the latter for the purpose of condensing the liquid products coming from the reaction.

The nitrating agent is recovered from the effluent gaseous mixture exempt from condensed liquid products, by absorption of the nitrogen oxides. The methane which has not reacted and the inert constituents produced in the course of the reaction, essentially CO and $CO_2$, may be partly recycled to the nitration reaction after recompression and the addition of a supply of starting material gas rich in methane, and partly evaporated for the purpose of their use as a fuel either in the unit itself or in a neighbouring unit consuming thermal energy.

The gaseous effluent used as fuel is drawn off at a regulated flow so as to maintain the content of the inert constituents in the reactive mixture constant.

The liquid phase issuing from the reaction is denitrated by treatment with an oxygenated gas for the purpose of the oxidation of the nitrogen oxides and for the recovery and recycling of the nitrating agent after concentration.

The fraction of nitrating agent recovered from the effluent gaseous phase after condensation and the fraction recovered from the effluent liquid phase are united, and the nitrating agent charge is completed with an addition of fresh agent which charge is passed to the nitration reactor.

The mixture of nitroparaffins having a high content of nitromethane is recovered from the denitrated liquid phase, then treated, and the active agent separated in the form of hydracid may be recycled to the nitration reaction after addition to the nitrating agent.

Figure 2:
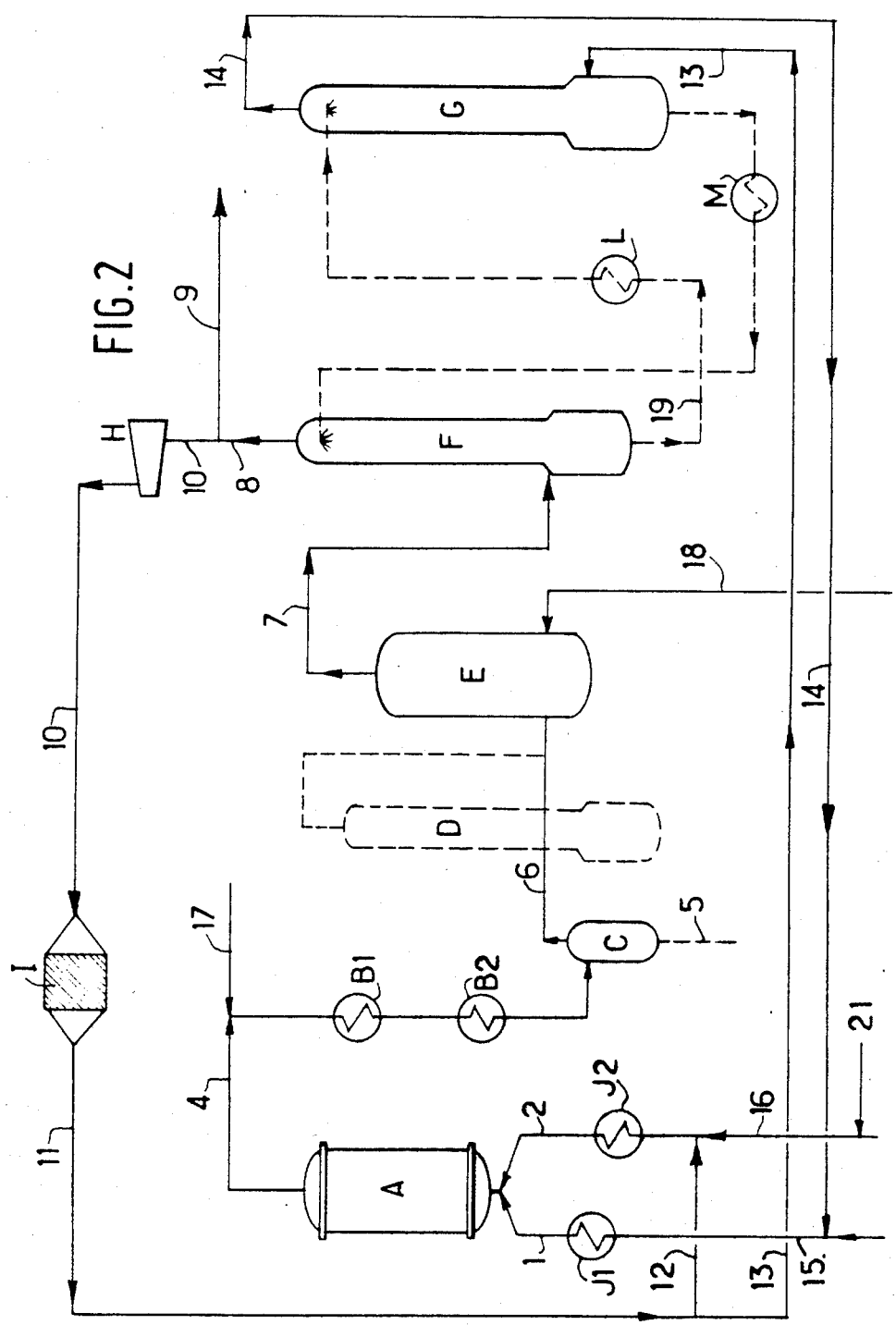

FIGS. 1 and 2 are flow diagrams showing preferred embodiments of the present invention.

An industrial unit for manufacturing nitromethane operating with nitric acid according to the process described is shown in FIG. 1 of the accompanying drawing. In the illustrated case, nitric acid is designated as the nitrating agent and hydrochloric acid is the active agent, and the inert constitutents, essentially carbon monoxides, are produced in the course of the nitration. The installation operates with a recycling of the methane which has not reacted, the nitrating and active agents and the inert constitutents.

The gas methane 1c and containing a controlled quantity of inert constituents is preheated in the exchanger-heater 2. The nitric acid 3 of the required concentration is vaporized and then superheated in the exchangers 4a and 4b. This current of nitric acid is formed by the two fractions of nitric acid recovered and united at 6 and an additional supply of $NO_3H$ 7.

The two currents of reagents 1 and 3, methane+inert constitutents and nitric acid+hydrocloric acid, are mixed in a homogeneous gaseous phase in the mixer 7 before being introduced in the nitration reactor 8.

The effluents 9 of the reactor are cooled in the heat exchangers 10a and 10b so as to effectively ensure the condensation of the liquid products. The exchanger 10a may be advantageously formed by a recuperation boiler adapted to recover a part of the thermal energy of the effluents.

The effluent gaseous phase is then separated from the effluent liquid phase in the separation zone formed by the separator 11.

The effluent gaseous phase 12a is sent to the zone absorbing the nitrogen oxides constituted by the absorption column 13 which operates in accordance with the known principles of absorption of $NO_x$ employed in nitric acid installations. The nitrogen oxides contained in the gaseous mixture 12a are transformed in the presence of an oxygenated gas, air or oxygen 14-14a into a nitric acid 5a of required concentration recovered at the base of the colum 13, while the required flow of water for obtaining the fixed concentration is admitted at 15 at the top of said column.

In order to obtain at the foot of the column 13 an acid of a sufficiently high concentration, it is advantageous to effect a prior oxidation of the gaseous mixture before it is introduced in the absorption column 13. This oxidation of the lower nitrogen oxides with an oxygenated gas 14c (air-oxygen or superoxygenated air) can be carried out in an oxidation tower 12b of the type of those employed in nitric acid installations.

The gases containing the methane which has not reacted, the inert constituents introduced at 1c and the inert constitutents produced in the course of the nitration process, are recovered from the top of the absorption column of the nitrogen oxides at 16.

A part 17 of this gaseous mixture is recompressed in the compressor 18 and sent back through the line 1b to the nitration zone after having received the addition 1a of gas rich in methane. The other part 19 of the gaseous mixture is discharged at a rate of flow so determined as to maintain constant the content of the inert constituents in the mixture 1c sent to the nitration.

The liquid phase issuing from the separator 11 is sent through the conduit 20 to the top of an oxidation zone of the nitrogen oxides dissolved into nitric acid, constituted by the column 21 in which the liquids are in contact in a counter-current manner with the oxygenated gas 14b. An effective condensation of the residual vapours of oxidation 22 in the exchanger 23 enables the entrainment of the nitromethane to be limited; the residual gases are discharged at 24 and the liquid phase 25a separated out in the separator 26.

The liquid phase devoid of nitrogen oxides $NO_x$ is received through the line 25b at the base of the column 21. The two fractions of the liquid phase rich in nitroparaffins are united in the line 25c.

This liquid phase 25c denitrated in this way is conveyed to the distillation column 26 where the nitromethane, or the mixture of nitroparaffins having a high content of nitromethane, is recovered at the top 27 in the form of an azeotropic mixture with the water, at atmospheric pressure, after cooling in the cooler 28. A part of the condensed fraction may be returned to the top of the column 26.

The hydrochloric acid contained in the liquid phase 25c is received at the foot of the column in the liquid 29 with the water-nitric acid mixture owing to an appropriate and controlled adjustment of the operation of the column separating the nitroparaffins.

If an organic chloride is used as an active agent, the latter is partly in the form of hydrochloric acid at the outlet of the reactor. This acid is received at the foot of the column in the liquid 29 with the water/nitric acid mixture owing to an appropriate adjustment of the ni-troparaffin separating column. The non-transformed part of the organic chlorides is recovered either at the top of the column or at the foot of the column, depending on the boiling temperature. This separated chloride may be recycled.

The liquid 29 drawn off at the foot of the distillation column 26 is subjected in the distillation column 30 to a distillation under atmospheric pressure so as to eliminate the water formed in the course of the reaction at the top of the column 31. After cooling in the cooler 32, the steam is discharged; a fraction may be recycled to the top of the column 30.

The nitric acid which has been reconcentrated is received at the foot of the column 30 at a concentration of 65% by weight through the conduit 33.

Depending on the composition of the hydrocarbon rich in methane employed, the reaction results in the formation of a certain quantity of heavy products which must be eliminated. For this purpose, all or a part of the reconcentrated nitric acid 33 is distilled in the column 34. The heavy products are received at the foot of the column 35.

The nitric acid 5a issuing from the absorption column of the nitrogen oxides 13, the nitric acid 33 issuing from the concentration column 30 and the acid 38 issuing from the column 34 are mixed, and, after addition of the additional nitric acid 6, are recycled to the reactor.

In order to obtain an acid for recycling at a sufficient concentration and for the purpose of economizing a part of the energy dissipated in the heating of the distillers of the columns 30 and 34, it is advantageous to draw off a part of the diluted nitric acid 29 and introduce it at the appropriate level of the absorption column 13 while reducing the flow of water 15 at the top of the column.

Studies have been made of the dynamic and static aspects of the influence of the various parameters affecting the degree of conversion of the methane into nitromethane.

Table I shows the results of the dynamic study and table II permits the comparison under static conditions of the influence of the various halogenated compounds on the conversion of the methane.

TABLE I

| Nitration of the methane (dynamic) | | | | | | | | | |
|---|---|---|---|---|---|---|---|---|---|
| Volume of the reactor (c.c.) | | | | 106 | | | | 250 | |
| Temperature °C. | | | | 390 | | | | 370 | |
| Flow of $CH_4$ (Nl/h) | | | | 2.52 | | | 1.7 | 3.1 | 4.5 | 2.4 |
| Flow of the mixture $HNO_3HCl$/c.c./h | | | | 9.5 | | | 13.1 | 11.8 | 8.5 | 8.8 |
| % vol. of aqueous solution of HCl (at 37% weight) in the mixture $HNO_3$ solution of HCl | 0 | 1 | 2 | 5 | 10 | 5 | 5 | 5 | 5 |
| ($CH_4$/$HNO_3$) mol. | 0.50 | 0.50 | 0.51 | 0.52 | 0.55 | 0.26 | 0.52 | 1.04 | 0.54 |
| (HCl/$HNO_3$) mol. % | 0 | 0.5% | 1.% | 2.7% | 5.6% | 2.7% | 2.7% | 2.7% | 2.7% |
| Duration of stay (seconds) | 20.8 | 20.5 | 19.5 | 19.3 | 18 | 40.4 | 37.8 | 40.1 | 50.2 |
| Pressure (bar absolute) | 1 | 1 | 1 | 1 | 1 | 1 | 1 | 1 | 1 |
| % CONVERSION OF $CH_4$ INTO NITRO METHANE | 2.1 | 7.4 | 14.1 | 15.6 | 18.4 | 21.5 | 16.4 | 6. | 18.7 |

This table I shows the influence of the ratio $CH_4/HNO_3$.

TABLE II

| Experiments carried out in static reactors NITRATION OF THE METHANE IN THE PRESENCE OF DIFFERENT ACTIVE AGENTS NITRATING AGENT = $HNO_3$ or $NO_2$ | | | | | | | | | | | | | | |
|---|---|---|---|---|---|---|---|---|---|---|---|---|---|---|
| Vol. of the reactor (c.c.) | | 700 | | | 950 | 700 | 950 | 700 | | | | | 950 | |
| Initial pressure (mm. Hg)** | 660 | 700 | 720 | 700 | 700 | 640 | 770 | 700 | 720 | 750 | 670 | 670 | 660 |
| TEMPERATURE (°C.) | | | | | | | | 400° C. | | | | | | |
| Duration of stay (min.) | | | | | | | | 5 mn | | | | | | |
| $CH_4$ introduced c.c. N.T.P. | 120 | 100 | 100 | 120 | 120 | 120 | 120 | 120 | 120 | 120 | 120 | 120 | 120 |

TABLE II-continued

Experiments carried out in static reactors
NITRATION OF THE METHANE IN THE PRESENCE OF DIFFERENT ACTIVE AGENTS
NITRATING AGENT = HNO₃ or NO₂

| | | | | | | | | | | | | | |
|---|---|---|---|---|---|---|---|---|---|---|---|---|---|
| $NO_2$ introduced c.c. liq. | | | 0.24 | 0.2 | | | 0.35 | 0.18 | 0.18 | | | | |
| $HNO_3$ 100% introduced c.c. liq. | 0.24 | 0.3 | | | 0.4 | 0.2 | | | | 0.4 | 0.4 | 0.4 | 0.4 |
| ACTIVE AGENT: Nature | — | — | — | — | HCl | HCl | HCl | HCl | HCl | HCl | $CH_2Cl_2$ | $CH_2Cl_2$ | $CH_2Cl_2$ |
| $CH_4$/Nitrating Agent (mol.) | 0.94 | 0.63 | 0.60 | 0.85 | 0.56 | 1.08 | 0.48 | 0.94 | 0.94 | 0.56 | 0.56 | 0.56 | 0.56 |
| Active Agent/Nitrating Agent (% mol.) | — | — | — | — | 2.5 | 2.5 | 2.2 | 2.1 | 4.2 | 5.1 | 2.9 | 4.1 | 1.6 |
| Conversion of the methane into nitromethane (%) | 3.1 | 5.7 | 5.1 | 3.6 | 26. | 6.8 | 26.9 | 16.1 | 17.2 | 25.4 | 23.4 | 25.6 | 22.2 |

| | | | | | | | | |
|---|---|---|---|---|---|---|---|---|
| Vol. of the reactor (c.c.) | | 950 | | | 700 | | 700 | |
| Initial pressure (mm Hg)** | 600 | 600 | 550 | 560 | 600 | 570 | 600 | 600 |
| Temperature (°C.) | | 360 | | | 380 | | 380 | |
| Duration of stay (min.) | | 5 mn | | | 5 mn | | 5 mn | |
| $CH_4$ introduced c.c. N.T.P. | 100 | 100 | 50 | | 50 | | 50 | |
| $HNO_3$ introduced c.c. liq. | 0.4 | 0.4 | 0.3 | | 0.3 | | 0.3 | |
| ACTIVE AGENT: Nature | $Cl_2$ | $Br_2$ | | | $CH_2Cl_2$ | | $CCl_2=CCl_2$ | $CHCl=CHCl$ |
| Solvent used: Nature | — | — | | | Methanol | | Methanol | Methanol |
| Vol. active agent in the sol. | 100% | 100% | | 100% | 10% | 40% | 20% | 20% |
| Vol. solution introduced (c.c.) | 4 cm³ gas | 0.02 | 0.02 | 0.02 | 0.04 | 0.02 | 0.04 | 0.04 |
| $CH_4/HNO_3$ (mol.) | 0.47 | 0.47 | 0.31 | | 0.31 | | 0.31 | 0.31 |
| Active agent/Nitrating Agent (mol.) | 1.9 | 4.1 | 5.4 | 4.3 | 0.9 | 1.7 | 1.1 | 1.4 |
| Conversion of the methane into nitromethane (%) | 22.6 | 5.5 | 5.9 | 26. | 20.5 | 28.2 | 30.4 | 28.8 |

**Calculated according to the quantities of reagents introduced and the temperature of the reactor.

Table III shows the results of the study of the nitration of the methane (dynamic) by nitric acid under pressure in the presence of various active agents or accelerators.

TABLE III

| Nitrating agent | $HNO_3$ (concent: 65 to 90%) | | | | | |
|---|---|---|---|---|---|---|
| Temperature °C. | 375 | 365 | 380 | 390 | 390 | 382 |
| Stoichiometry | 0.26 | 0.30 | 0.24 | 0.22 | 0.28 | 0.18 |
| Pressure (bar abs.) | 4 | 4 | 4 | 5 | 7 | 7 |
| Concentration % | 34 | 30.5 | 41.4 | 42.1 | 40.6 | 40.9 |
| Catalysis % | 2.9 | 4.9 | 1.4 | 1.01 | 1.24 | 0.7 |
| Duration of stay in seconds | 11.4 | 11.1 | 12.2 | 11.7 | 9.9 | 9.7 |
| Nature of the accelerator | $C_3H_7Cl$ | $C_3H_7Cl$ | $C_3H_7Cl$ | $C_2H_4Cl_2$ | $C_2H_4Cl_2$ | $C_2H_4Cl_2$ |
| Yield of $NC_1$ | 10.8% | 8.95% | 8.15% | 12.7% | 16.1% | 15.8% |

Stoichiometry denotes the molar ratio hydrocarbons/nitrating agent at the inlet of the reactor; the term concentration denotes the concentration of the reagents expressed as molar $$\% = \left[ \frac{\text{hydrocarbon flow} + \text{HNO}_3 \text{ flow}}{\text{total gas flow}} \right] \times 100;$$

the term catalysis (expressed in %) represents the quantity of accelerator employed:

$$\text{catalysis} = \frac{\text{accelerator in moles}}{(\text{hydrocarbons} + \text{NO}_2) \text{ moles}} \times 100;$$

and the yield in % denotes the percentage of methane transformed into $$\frac{NC_1 \text{ formed (moles)}}{\text{methane introduced (moles)}} \times 100.$$

A series of tests of nitration (dynamic) of methane with nitrogen peroxide were carried out by using a reactor of 386 c.c. internal volume formed by a tube having a diameter of 8/10 mm and a length of 10 m. The reagents: hydrocarbon and solution of the accelerator $NO_2$ and nitrogen are preheated to 135° C. and mixed at the inlet of the reactor.

As the accelerator is isopropyl chloride, a study was made of the influence of the catalysis, the results of which are given in table IV.

TABLE IV

| Influence of the Catalysis | | | |
|---|---|---|---|
| Nitrating agent $NO_2$ | Accelerator: isopropyl chloride | | |
| Temperature °C. | 344 | 360 | 375 |
| Stoichiometry | | 0.88 | |
| Pressure bar | | 9.7 | |
| Concentration % | | 80 | |
| Catalysis % | 1.43 | 0.89 | 0.69 |
| Duration of stay (s) | 8.7 | 8.4 | 8.3 |
| Yield of $NC_1$ % | 6.84 | 7.4 | 8.1 |

It was thus possible to observe that an increase in the temperature advantageously compensates for a drop in the catalysis.

The influence of the temperature was studied within the framework of the nitration of $CH_4$ by $NO_2$ in the presence of isopropyl chloride.

TABLE V

| Influence of the Temperature | | | |
|---|---|---|---|
| Temperature °C. | 360 | 375 | 400 |
| Stoichiometry | 0.88 | 0.5 | 0.2 |
| Pressure 1 bar abs. | | 11,2 | |
| Concentration % | | 70% | |
| Catalysis % | 0.71 | 0.62 | 0.63 |
| Duration of stay (s) | 8.4 | 8.4 | 8 |

TABLE V-continued

| Influence of the Temperature | | | |
| --- | --- | --- | --- |
| Yield of $NC_1$ % | 5.4 | 10.2 | 26.7 |

The results given in this table show that the decrease in the stoichiometry of from 0.88 to 0.2 associated with an increase in the temperature of from 360° to 400° C. results in an improved yield.

The influence of the pressure was studied in the nitration of methane with nitrogen peroxide in the presence of isopropyl chloride.

TABLE VI

| Influence of the Pressure | | | |
| --- | --- | --- | --- |
| Temperature °C. | 387 | 386 | 393 |
| Stoichiometry | | 0.3 | |
| Pressure 1 bar abs. | 11 | 15.6 | 24.7 |
| Concentration % | 70 | 50 | 30 |
| Catalysis | 0.67 | 0.62 | 0.62 |
| Duration of stay (s) | | 8 | |
| Yield of $NC_1$ % | 16.6 | 19.1 | 20.4 |

It is clear that the increase in pressure, associated with a decrease in the concentration, results in a greater increase in the selectivity.

A study was then made of the influence of the nature of the accelerator within the framework of the nitration of the methane by nitrogen peroxide.

TABLE VII

| Influence of the Nature of the Accelerator | | | | | |
| --- | --- | --- | --- | --- | --- |
| Nature of the accelerator | Isopropyl chloride | 1-2 dichloro ethane | | Carbon tetrachloride | |
| Temperature °C. | 388 | 396 | 397 | 398 | 398 |
| Pressure (bar) | 19.8 | 18.6 | 19 | 18.9 | 18.8 |
| Duration of stay (s) | 8.3 | 7.8 | 7.8 | 8.1 | 8.1 |
| Concentration % | 40 | 40 | 40 | 40 | 40 |
| Stoichiometry | 0.3 | 0.3 | 0.3 | 0.3 | 0.3 |
| Catalysis % | 0.53 | 0.20 | 0.27 | 0.12 | 0.10 |
| Yield of $NC_1$ % | 17.6 | 19.2 | 23.3 | 20.7 | 18.5 |

It was possible to observe that the effectiveness of a chlorinated accelerator is due to the number of chlorine atoms it contains.

An industrial unit for nitrating methane with nitrogen peroxide and possibly with a nitric acid and nitrogen peroxide mixture, is shown in FIG. II of the accompanying drawing. In the illustrated embodiment, the installation operates under pressure and tests giving satisfactory results were in particular carried out at a pressure of 19 bars. The active agent is a halogenated derivative.

The additional methane added through the supply circuit 16 joins the gas recycled through the recuperation circuit 12 before being preheated in the heater $J_2$. In a suitable mixer (not shown) there is effected the mixture which is as homogeneous as possible of the gas 2 rich in methane, to which is added the chlorinated derivative employed as an active agent introduced through the supply circuit 21, and the gas 1 rich in nitrogen peroxide. This operation is carried out in the immediate vicinity of the reactor A. This reactor may be of the type having a bundle of tubes in contact with a fluid having a high thermal exchange capacity.

The effluents 4 of the reactor are quenched with the water 17 and cooled in the coolers $B_1$ and $B_2$ so as to condense the liquid constituents which are separated out in the separator C from the gaseous phase 6. The liquid mixture 5 is sent to the washing and distillation installation where the nitromethane will be recovered together with the nitric acid present in the liquid phase. The gaseous effluent 7 optionally washed with water in the washer D is sent to the oxidation tower E where, after addition of the gas 18 rich in oxygen (air, oxygen or superoxygenated air), the nitrogen monoxide NO contained therein is converted into nitrogen peroxide $NO_2$ which is absorbed in the absorption column F in a suitable conventional solvent such as nitric acid.

The gaseous current 8 is then separated into two fractions. One of the fractions, the line 9, constitutes the purge of the loop for discharging the inert constitutents produced or introduced; the rate of flow of this purge increases with the quantity of inert constitutents contained in the gas 18. The purged gases 9 may be used as fuels (in a boiler for example) after the $NO_2$ still contained in an absorption column has been recovered.

The other fraction 10 of the gaseous stream 8 is recompressed in the compressor at H for its return to the reactor. In order to avoid sending with the reagents a quantity of oxygen such as the excess oxygen resulting from the conversion at E of the NO into $NO_2$ which would have an adverse effect on the nitration, the gas 10 is subjected to a selective catalytic oxidation in the catalytic oxidizer I so as to burn a part of the methane contained in the gas 10.

The gas 11 issuing from the oxidizer I is then divided into two fractions. The first fraction 12 receives the addition of methane or gas rich in methane: natural gas, refinery gas 16, and returned directly to the following reactor 2.

The other fraction 13 is used for ensuring the desorption of the $NO_2$ dissolved in the solution 19 sent, after heating in the heater L, to the desorption column G. The gas rich in $NO_2$ issuing from the column G through the recuperation circuit 14 receives the addition of $NO_2$ through the supply circuit 15 before returning to the reactor through the pipe 1. The solution 20 containing less $NO_2$ which has dissolved is cooled in the cooler M before being used again in the absorber F.

What is claimed is:

1. A process for preparing nitromethane by nitration in a homogeneous gaseous phase reaction medium of methane or a mixture of hydrocarbons containing a substantial quantity of methane, the nitrating agent being selected from the group consisting of nitric acid, nitrogen peroxide and mixtures thereof, the molar ratio methane/nitrating agent being between 0.1 and 5, the reaction contact time being between 0.1 and 120 seconds, the reaction pressure being between 1 and 35 bars absolute, the reaction temperature being between 270° and 600° C. and wherein the nitration reaction is carried out in the presence of an active agent introduced in a molar ratio of active agent/methane at the most equal to 3 and a molar ratio of active agent/nitrating agent at the least equal to about 1, the active agent being selected from the group consisting of a halogen, a hydracid, and an organic halide vaporizable or soluble in the reaction medium.

2. A process according to claim 1, wherein said molar ratio of methane to nitrating agent is between 0.2 and 2.

3. A process according to claim 1, wherein said reaction contact time is between 1 and 30 seconds.

4. A process according to claim 1, wherein said reaction pressure is between 2 and 10 bars when said nitrating agent is nitric acid.

5. A process according to claim 1, wherein said reaction pressure is between 5 and 30 bars when said nitrating agent is nitrogen peroxide.

6. A process according to claim 1, wherein said reaction temperature is between 300° and 480° C.

7. A process according to claim 1, wherein the nitration reaction is carried out in the presence of a compound carrying an NO group or an $NO_2$ group, or a compound selected from the group consisting of an aldehyde, a ketone and an alcohol.

8. A process according to claim 1, wherein at least one constitutent which is inert with respect to the reaction and the reactive products is added.

9. A process according to claim 1, wherein said mixture of hydrocarbons containing a substantial quantity of methane is natural gas or refinery gas.

10. A process according to claim 1 wherein said active agent is selected from the group consisting of hydrochloric acid, methylene chloride, trichloromethane, ethyl chloride, propyl chloride, isopropyl chloride, benzyl chloride, dichloro and tetrachloroethylene, mono-, di- and trichlorethane, and carbon tetrachloride.

11. A process for preparing nitromethane by nitration of methane, comprising:

preheating methane containing at least one constituent which is inert with respect to the reaction and the reaction products;

independently preheating a nitrating agent selected from the group consisting of nitric acid, nitrogen peroxide and mixtures thereof;

incorporating in the methane or the nitrating agent prior to said preheating thereof an active agent selected from the group consisting of a halogen, a hydracid and an organic halide vaporizable or soluble in a subsequently formed reaction medium;

forming a homogeneous gaseous phase reaction medium of said methane, said inert constituent, said active agent and said nitrating agent as quickly as possible after said preheating, the molar ratio of methane to nitrating agent being 0.1 and 5, the reaction pressure being between 1 and 35 bars absolute, the reaction temperature being between 270° and 600° C., and the molar ratio of said active agent to methane being at most equal 3, and effecting nitration of said methane in said homogeneous gaseous phase reaction medium for a time of 0.1 to 120 seconds;

cooling reaction effluents to obtain a gaseous phase and a liquid phase, and separating said liquid phase from said gaseous phase;

recompressing methane which has not reacted and inert constituents produced during the nitration reaction, adding thereto a fresh supply of methane, and recycling the resultant mixture to the reaction zone;

recovering the nitrating agent by absorption of nitrogen oxides from said gaseous phase;

denitrating the liquid phase by treatment with an oxygenated gas, concentrating and recovering the nitrating agent;

uniting fractions of nitrating agent recovered from the gaseous and liquid effluent phases; and recovering a mixture of nitroparaffins having a high content of nitromethane from the denitrated liquid phase, and washing and purifying the mixture of nitroparaffins.

12. A process according to claim 11, when the nitrating agent is nitric acid, comprising uniting the fractions of nitrating agent recovered from the gaseous and liquid effluent phases and recycling said fractions of nitrating agent to the reaction zone, after adding thereto an added amount of nitrating agent.

13. A process according to claim 11, when the active agent is a hydracid, comprising adding said active agent in the nitrating agent and preheating said active agent in the presence of said nitrating agent, recovering said active agent after the nitration reaction from the denitrated effluent liquid phase and recycling it.

14. A process according to claim 13 wherein said hydracid is hydrochloric acid.

15. A process according to claim 11, when the active agent is a halogenated organic compound, comprising adding said agent in said gas rich in methane and preheating it in the presence of said gas rich in methane, and recycling the hydrochloric acid issuing from its conversion in the course of the nitration with the nitric acid returned to the reactor, while separating and then recycling the non-converted organic chloride.

16. A process according to claim 15 wherein said halogenated organic compound is an organic chloride.

17. A process according to claim 11, when the nitrating agent is nitrogen peroxide, comprising compressing and subjecting to a selective catalytic oxidation a fraction of the gaseous effluent issing from the absorption of the nitrogen peroxide, a fraction of said oxidized effluent ensuring the desorption of the dissolved nitrogen peroxide.

* * * * *